(12) United States Patent
Reddy et al.

(10) Patent No.: US 7,805,979 B2
(45) Date of Patent: Oct. 5, 2010

(54) HIGH ACCURACY CONTAMINATION ESTIMATION IN HYDROCARBON SAMPLES USING GC×GC

(75) Inventors: Christopher Michael Reddy, East Falmouth, MA (US); Oliver C. Mullins, Ridgefield, CT (US); Bhavani Raghuraman, Wilton, CT (US); Robert K. Nelson, Mashpee, MA (US)

(73) Assignees: Schlumberger Technology Corporation, Cambridge, MA (US); Woods Hole Oceanographic Institution, Woods Hole, MA (US)

( * ) Notice: Subject to any disclaimer, the term of this patent is extended or adjusted under 35 U.S.C. 154(b) by 186 days.

(21) Appl. No.: 11/876,185

(22) Filed: Oct. 22, 2007

(65) Prior Publication Data

US 2008/0105032 A1 May 8, 2008

Related U.S. Application Data

(60) Provisional application No. 60/862,879, filed on Oct. 25, 2006.

(51) Int. Cl.
G01N 30/02 (2006.01)
(52) U.S. Cl. .................................... 73/23.38
(58) Field of Classification Search ................. 73/23.41
See application file for complete search history.

(56) References Cited

U.S. PATENT DOCUMENTS 6,274,865 B1 8/2001 Schroer et al.
6,350,986 B1 2/2002 Mullins et al.

FOREIGN PATENT DOCUMENTS

WO 2007071634 A1 6/2007

OTHER PUBLICATIONS

Patel, Choosing the Right Synthetic-Based Drilling Fluids: Drilling Performance Versus Environmental Impact, SPE 39508, 1998, pp. 95-108.
Churan et al., Onsite and Offsite Monitoring of Synthetic-Based Drilling Fluids for Oil Contamination, SPE 37906, pp. 179-192, 1997.
Gozalpour et al., Predicting Reservoir Fluid Phase and Volumetric Behaviour from Samples Contaminated with Oil-Based Mud, SPE 56747, pp. 1-9, 1999.
Reddy et al., The West Falmouth Oil Spill after Thirty Years: The Persistence of Petroleum Hydrocarbons in Marsh Sediments, Environmental Science & Technology, vol. 36, No. 22, 2002, pp. 4754-4760.

(Continued)

*Primary Examiner*—Hezron Williams
*Assistant Examiner*—Mark Shabman
(74) *Attorney, Agent, or Firm*—James McAleenan; Vincent Loccisano; Brigid Laffey

(57) ABSTRACT

A method of estimating contamination of oil based mud filtrate in a hydrocarbon sample. The method comprising the steps of obtaining a hydrocarbon sample contaminated with oil based mud filtrate, then analyzing the contaminated hydrocarbon sample using two-dimensional gas chromatography (GC×GC). The method further comprises identifying one or more unique component or tracer in the oil based mud filtrate in the contaminated hydrocarbon sample. Finally, the method comprises of summing the peak volumes of the one or more unique component or tracer, relative to the peak volumes of a clean hydrocarbon sample.

22 Claims, 5 Drawing Sheets

OTHER PUBLICATIONS

Nelson et al., Tracking the Weathering of an Oil Spill with Comprehensive Two-Dimensional Gas Chromatography, Environmental Forensics, vol. 7, 2006, pp. 33-44.

Van Deursen et al., Group-Type Identification of Oil Samples Using Comprehensive Two-Dimensional Gas Chromatography Coupled to a Time-of-Flight Mass Spectrometer (GC×GC-TOF), J. High Resol. Chromatogr., vol. 23, 2000, pp. 507-510.

Phillips et al., Comprehensive two-dimensional gas chromatography: a hyphenated method with strong coupling between the two dimensions, Journal of Chromatography A, vol. 856, 1999, pp. 331-347.

Frysinger et al., Determination of Oxygenates in Gasoline by GC×GC, J. High Resol. Chromatogr., vol. 23, No. 3, 2000, pp. 197-201.

Frysinger et al., Quantitative Determination of BTEX and Total Aromatic Compounds in Gasoling by Comprehensive Two-Dimensional Gas Chromatography (GC×GC), J. High Resol. Chromatogr. vol. 22, No. 4, 1999, pp. 195-200.

Frysinger et al., Separation and identification of petroleum biomarkers by comprehensive two-dimensional gas chromatography, J. Sep. Sci. vol. 24, 2001, pp. 87-96.

Frysinger et al., GC×GC—A New Analytical Tool for Environmental Forensics, Environmental Forensics, vol. 3, 2002, pp. 27-34.

Reddy, Identification and quantification of alkene-based drilling fluids in crude oils by comprehensive two-dimensional gas chromatography with flame ionization detection, Journal of Chromatography A, vol. 1148, 2007, pp. 100-107.

Hiatt et al., Identification and Quantification of Diesel Fuel Components Derived from Off-Shore Drilling Operation Discharges, Journal of High Resolution Chromatography & Chromatography Communications, vol. 8, 1985, pp. 4-7.

Schoenmakers, et al., Comparison of comprehensive two-dimensional gas chromatography and gas chromatography-mass spectrometry for the characterization of complex hydrocarbon mixtures, Journal of Chromatography A, vol. 892, 2000, pp. 29-46.

Kromidas, More Practical Problem Solving in HPLC, Wiley, XP-002472815, 2005, p. 233.

Wenger, et al., Impact of modern deepwater drilling and testing fluids on geochemical evaluations, Organic Geochemistry, vol. 35, 2004, pp. 1527-1536.

Muhlen, et al., Applications of comprehensive two-dimensional gas chromatography to the characterization of petrochemical and related samples, Journal of Chromatography A, vol. 1105, 2006, pp. 39-50.

Vendeuvre, et al., Multidimensional gas chromatography for the detailed PIONA analysis of heavy naphtha: Hyphenation of an olefin trap to comprehensive two-dimensional gas chromatography, Journal of Chromatography A, vol. 1090, 2005, pp. 116-125.

Beens, et al., Quantitative Aspects of Comprehensive Two-Dimensional Gas Chromatography (GC×GC), J. High Resol. Chromatogr., vol. 21, 1998, pp. 47-54.

Beens, et al., Moving Cryogenic Modulator for the Comprehensive Two-Dimensional Gas Chromatography (GC×GC) of Surface Water Contaminants, J. Microcolumn Separations, vol. 13, No. 3, 2001, pp. 134-140.

HIGH ACCURACY CONTAMINATION ESTIMATION IN HYDROCARBON SAMPLES USING GC×GC

BACKGROUND OF THE INVENTION

1. Field of the Invention

The present invention relates in general to sampling and pressure-volume-temperature (PVT) analysis of hydrocarbon samples using two-dimensional gas chromatography (GC×GC).

2. Background of the Invention

The petroleum industry uses a variety of chemicals while drilling wells for the recovery of hydrocarbons from geologic reservoirs. Synthetic-based muds (SBM) and conventional (diesel/mineral) oil-based muds (OBM) as drilling fluids are becoming increasingly common because of the rapid drilling rates and increased hole stability associated with their use. This mud filtrate is usually present as a contaminant at some level in the collected hydrocarbon samples and alters the physical properties and phase behavior of the reservoir fluid samples. The level of contamination determines the extent to which the measured fluid properties will vary from actual. Collecting representative samples of hydrocarbons in an oil field for laboratory analysis for pressure-volume-temperature (PVT) labs is essential for determining gas-oil ratios, phase transition pressures, viscosities, composition and various other parameters, which is useful for building production facilities and for developing production strategies. Therefore, it is essential for laboratories to quantify the level of mud filtrate contamination very accurately in collected samples to understand and compensate for the effects of the contamination on the fluid properties of the original reservoir fluid.

The most common technique for quantifying contamination due to SBM/OBM filtrate is based on traditional one-dimensional gas chromatography with flame ionization detection (GC–FID), using "skimming" and "subtraction" methods. These methods are expensive in terms of number of analysis to be done. Moreover, one-dimensional gas chromatography usually has oil peaks which overlap with contamination peaks making determination difficult. In addition, one-dimensional gas chromatography can suffer at low levels of contamination where it is obscured by more dominant petroleum hydrocarbons, which may lead to low sensitivity as well as poor accuracy. Thus, one-dimensional gas chromatography of a typical contaminated crude oil does not provide sufficient resolution to determine unambiguously the amount of contamination. Thus, there remains a need in the art for new methods for accurately estimating contamination due to SBM/OBM filtrate in crude oil samples.

SUMMARY OF THE DISCLOSURE

The invention relates to methods utilizing comprehensive two-dimensional gas chromatography (GC×GC) which provide estimates of contamination from conventional oil based and synthetic oil based mud filtrates in hydrocarbon samples. The method according to the invention provides for a high-resolution technique that can be used to separate and analyze one or more unique components or added tracers in oil based mud filtrates that are not generally present in a clean hydrocarbon sample. Even if present in the clean hydrocarbon sample, the levels are such that they are undetectable using two-dimensional gas chromatography (GC×GC) on the clean crude hydrocarbons and hence do no affect the estimation of the contamination by two-dimensional gas chromatography (GC×GC) on contaminated hydrocarbon samples. Further, this high-resolution technique can provide for higher accuracy in the estimation of contamination in hydrocarbon samples as compared to traditional techniques that are based on one-dimensional gas chromatography.

According to an aspect of the invention, the invention can be directed to methods for estimating contamination of oil based mud filtrate in a hydrocarbon sample.

According to another embodiment of the present invention, the invention can be directed to a method of estimating contamination of oil based mud filtrate in a hydrocarbon sample. The method can comprise of the steps of obtaining a hydrocarbon sample contaminated with oil based mud filtrate and then analyzing the contaminated hydrocarbon sample using two-dimensional gas chromatography (GC×GC). The method can further comprise of the step of identifying one or more unique component or tracer in the oil based mud filtrate in the contaminated hydrocarbon sample. Finally, the method can comprise of the step of summing the peak volumes of the one or more unique component or tracer, relative to the peak volumes of a clean hydrocarbon sample.

According to an aspect of the present invention, the oil based mud filtrate may be selected from the group consisting of a non-synthetic oil based mud filtrate or a synthetic oil based mud filtrate.

According to an aspect of the present invention, at least one unique component of the one or more unique component can be from the synthetic oil based component. Further, the method may include at least one tracer of the one or more tracer that is added to the non-synthetic oil based mud filtrate. It is possible the method the contamination of oil based mud filtrate in the hydrocarbon sample can be greater than about 0.1%. Further still, the method can include the contamination of oil based mud filtrate in the hydrocarbon sample to be possibly from about 0.1% to about 10%.

According to an aspect of the present invention, two-dimensional gas chromatography (GC×GC) may have a greater resolving power in identifying one or more unique component and tracer when compared to a one-dimensional gas chromatography. Further, the method may include are at least two or more dimension separations. Further still, the GC×GC may involve a first dimension separation using a non-polar phase; and a second dimension separation using a polar phase. It is possible the non-polar phase separates petroleum compounds by volatility differences; and the polar phase separates first dimension co-eluters by polarity differences. The present invention may include the non-polar phase being a polydimethylsiloxane column; and the polar phase being a 50% phenyl-substituted polydimethylsiloxane column.

According to an aspect of the present invention, the unique component or tracer in the oil based mud filtrate may be selected from the group consisting of an iso-olefin, a liner alpha olefin, a poly-alpha olefin or ester. Further, it is possible the iso-olefin can be a $C_{16}$ to $C_{20}$ alkene.

According to another embodiment of the present invention, the invention can be directed to a method of separating and analyzing contamination of drilling fluid in a hydrocarbon sample. The method can include the steps of obtaining a hydrocarbon sample contaminated with drilling fluid and then analyzing the contaminated hydrocarbon sample using two-dimensional gas chromatography (GC×GC), wherein the contaminated hydrocarbon sample is subject to two different stationary phase selectivities. Further, the method may include the step of identifying one or more unique component or tracer in the drilling fluid in the contaminated hydrocarbon sample. Finally, the method can include the step of summing the peak volumes of the one or more unique component or tracer, relative to the peak volumes of a clean hydrocarbon sample.

According to an aspect of the present invention, the drilling fluid can be selected from the group consisting of a non-synthetic oil based mud filtrate or a synthetic oil based mud filtrate. Further, it is possible that the one or more unique component can be from the synthetic oil based mud filtrate. Further still, the method may include at least one tracer of the one or more tracer that is added to the non-synthetic oil based mud filtrate.

According to an aspect of the present invention, the two different stationary phase selectivities may involve a first dimension separation using a non-polar phase; and a second dimension separation using a polar phase. Further, the method may include the non-polar phase that separates petroleum compounds by volatility differences; and the polar phase separates first dimension co-eluters by polarity differences. Further still, the method may include the non-polar phase that is a polydimethylsiloxane column; and the polar phase is a 50% phenyl-substituted polydimethylsiloxane column.

According to an aspect of the present invention, the contamination of drilling fluid in the hydrocarbon sample may be greater than about 0.1%. Further, it is possible the unique component or tracer in the drilling fluid is selected from the group consisting of an iso-olefin, a liner alpha olefin, a poly-alpha olefin or ester. Further still, the method may include the iso-olefin being a $C_{16}$ to $C_{20}$ alkene.

According to another embodiment of the present invention, the invention can be directed to a method of estimating contamination of crude oil in a oil based mud filtrate sample. The method can comprise of the steps of obtaining an oil based mud filtrate sample contaminated with crude oil and then analyzing the oil based mud filtrate sample using two-dimensional gas chromatography (GC×GC). Further, the method can include the next step of identifying one or more unique component or tracer in the crude oil in the contaminated oil based mud filtrate sample. Finally, the method can include the summing the peak volumes of the one or more unique component or tracer, relative to the peak volumes of the oil based mud filtrate sample.

According to an aspect of the present invention, the GC×GC can involve a first dimension separation using a non-polar phase; and a second dimension separation using a polar phase.

Further areas of applicability of the present disclosure will become apparent from the detailed description provided hereinafter. It should be understood that the detailed description and specific examples, while indicating various embodiments, are intended for purposes of illustration only and are not intended to necessarily limit the scope of the disclosure.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein:

FIG. 3(a) shows the 1D-GC chromatogram of a hydrocarbon contaminated with drilling fluids. The shaded areas are alkenes that may be possibly derived from drilling fluid contamination of iso-olefins.

DETAILED DESCRIPTION OF THE PREFERRED EMBODIMENTS

Figure 1:
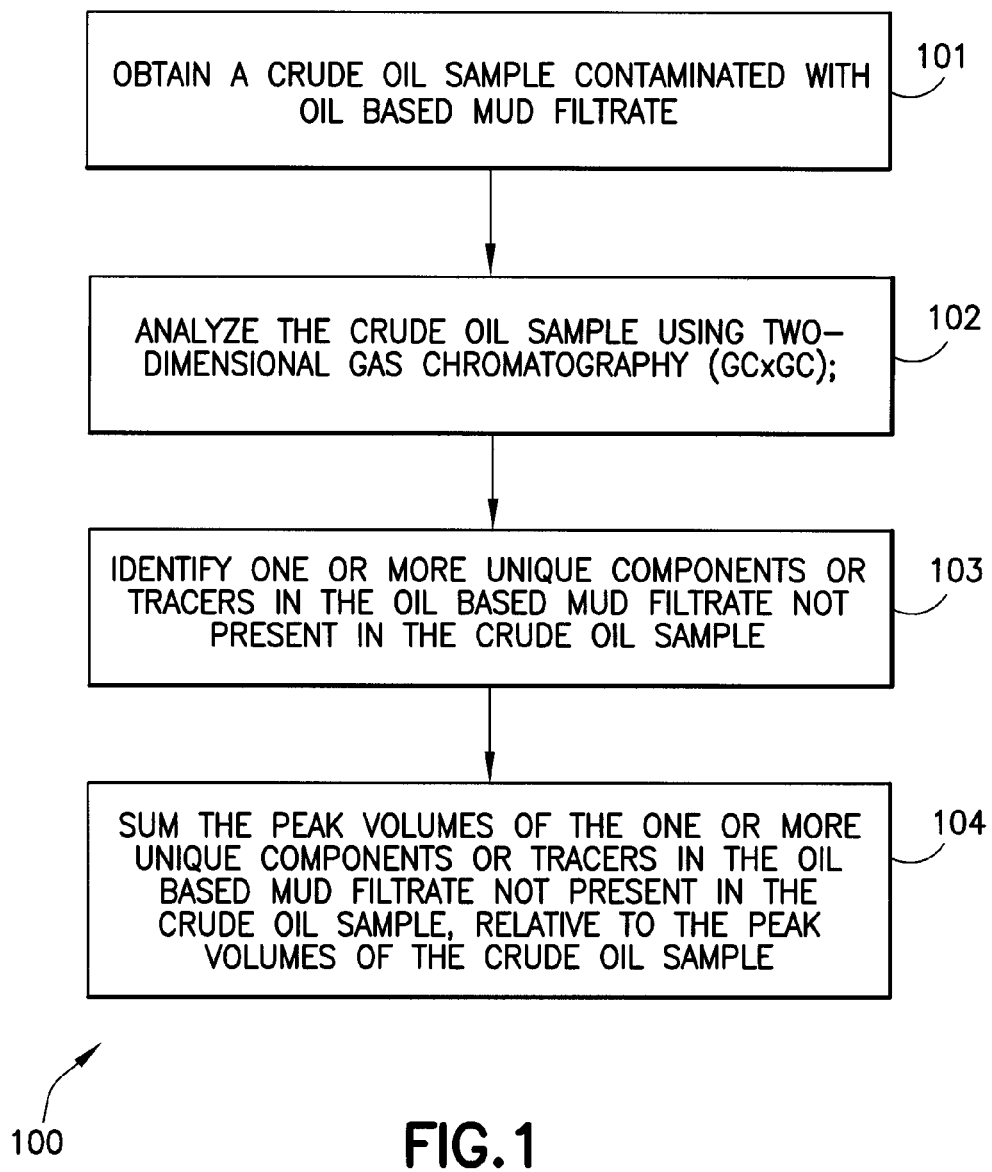
FIG. 1 shows a method according to an aspect of the invention for estimating the amount of contamination of oil based mud filtrate in a hydrocarbon sample.

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

The present invention is directed to methods for estimating contamination of oil based mud filtrate in a hydrocarbon sample. The method comprising obtaining the hydrocarbon sample contaminated with oil based mud filtrate. Further, the method provides for identifying the contamination in the hydrocarbon sample by separating and analyzing one or more unique components or added tracers in oil based mud filtrates that are not generally present in a clean hydrocarbon sample. Even if present in the clean hydrocarbon sample, the levels are such that they are undetectable using two-dimensional gas chromatography (GC×GC) on the clean crude hydrocarbons and hence do no affect the estimation of the contamination by two-dimensional gas chromatography (GC×GC) on contaminated hydrocarbon samples. Then the method provides for summing the peak volumes of the one or more unique components or added tracers in the oil based mud filtrate as discussed above in the contaminated hydrocarbon sample, relative to the peak volumes of the clean hydrocarbon sample.

According to an aspect of the invention, the expression "hydrocarbon", by non-limiting example, may refer to: unrefined petroleum, liquid petroleum and crude oil, among other things.

Further, the expression "petroleum", by non-limiting example, may refer to: a complex mixture of naturally occurring hydrocarbon compounds found in rock, among other things. Further for example, petroleum can range from solid to gas, but the term may generally be used to refer to liquid crude oil. Impurities such as sulfur, oxygen and nitrogen can be common in petroleum. Further still, there can be considerable variation in color, gravity, odor, sulfur content and viscosity, among other things in the petroleum depending on which geographical location the petroleum is taken.

Also, the expression "drilling fluid", by non-limiting example, may refer to any of a number of liquid and/or gaseous fluids and mixtures of fluids and solids (as solid suspensions, mixtures and emulsions of liquids, gases and solids) used in operations to drill boreholes into the earth. Synonymous with "drilling mud" in general usage, although some reserve the term "drilling fluid" for more sophisticated and well-defined "muds." Classifications of drilling fluids have been attempted in many ways through the world. For example, by non-limiting in scope, one classification scheme, given here, is based only on the mud composition by singling out the component that clearly defines the function and performance of the fluid: (1) water-base, (2) non-water-base and (3) gaseous (pneumatic). Each category has a variety of subcategories that can considerably overlap each other.

Further still, the term "mud", by non-limiting example, may generally be synonymous with "drilling fluid" and encompasses water based mud, non aqueous mud and gaseous mud.

It should also be noted that the phrase "non aqueous mud", by non limiting example, may refer to diesel and mineral oil based muds or synthetic base mud.

According to another aspect of the invention, the method involves using a comprehensive two-dimensional gas chromatography (GC×GC) that can provide for better analysis such as contamination analysis when analyzing petroleum hydrocarbons over the traditional one-dimensional gas chromatography method. GC×GC instruments produce high-resolution chromatographic separations because each petroleum compound is subjected to two different stationary phase selectivities. Most often, the first dimension separation uses a non-polar phase to separate petroleum compounds by volatility differences, and the second dimension uses a more polar phase to separate first dimension co-eluters by polarity differences. The resulting two-dimensional chromatogram can have thousands of resolved peaks sorted according to their volatility and polarity properties. A GC×GC chromatogram has compound peaks grouped by carbon number along the x-axis and by chemical class along the y-axis. For petroleum, this produces separated chemical classes such as alkanes, cycloalkanes, and one-, two-, and multi-ring aromatics, with additional groupings showing homologous series within each class.

Referring to FIG. 1, a method for estimating contamination of oil based mud filtrate in a hydrocarbon sample 100 is shown. First, a hydrocarbon sample contaminated with oil based mud filtrate is obtained 101. Next, the contaminated hydrocarbon sample is analyzed using two-dimensional gas chromatography (GC×GC) 102 in order to identify one or more unique components or tracers present in the oil based mud filtrate that are not generally present in a clean hydrocarbon sample. Finally, the peak volumes of the one or more unique components or tracers in the oil based mud filtrate are summed, relative to the peak volumes of the hydrocarbon sample 104. This method provides an estimate of the contamination of oil based mud filtrate in the hydrocarbon sample. Further, it should be noted that, even if small amounts of contamination are present in the clean hydrocarbon sample, the levels are such that they are undetectable using two-dimensional gas chromatography (GC×GC) on the clean crude hydrocarbons and hence do no affect the estimation of the contamination by two-dimensional gas chromatography (GC×GC) on contaminated hydrocarbon samples.

Figure 2:
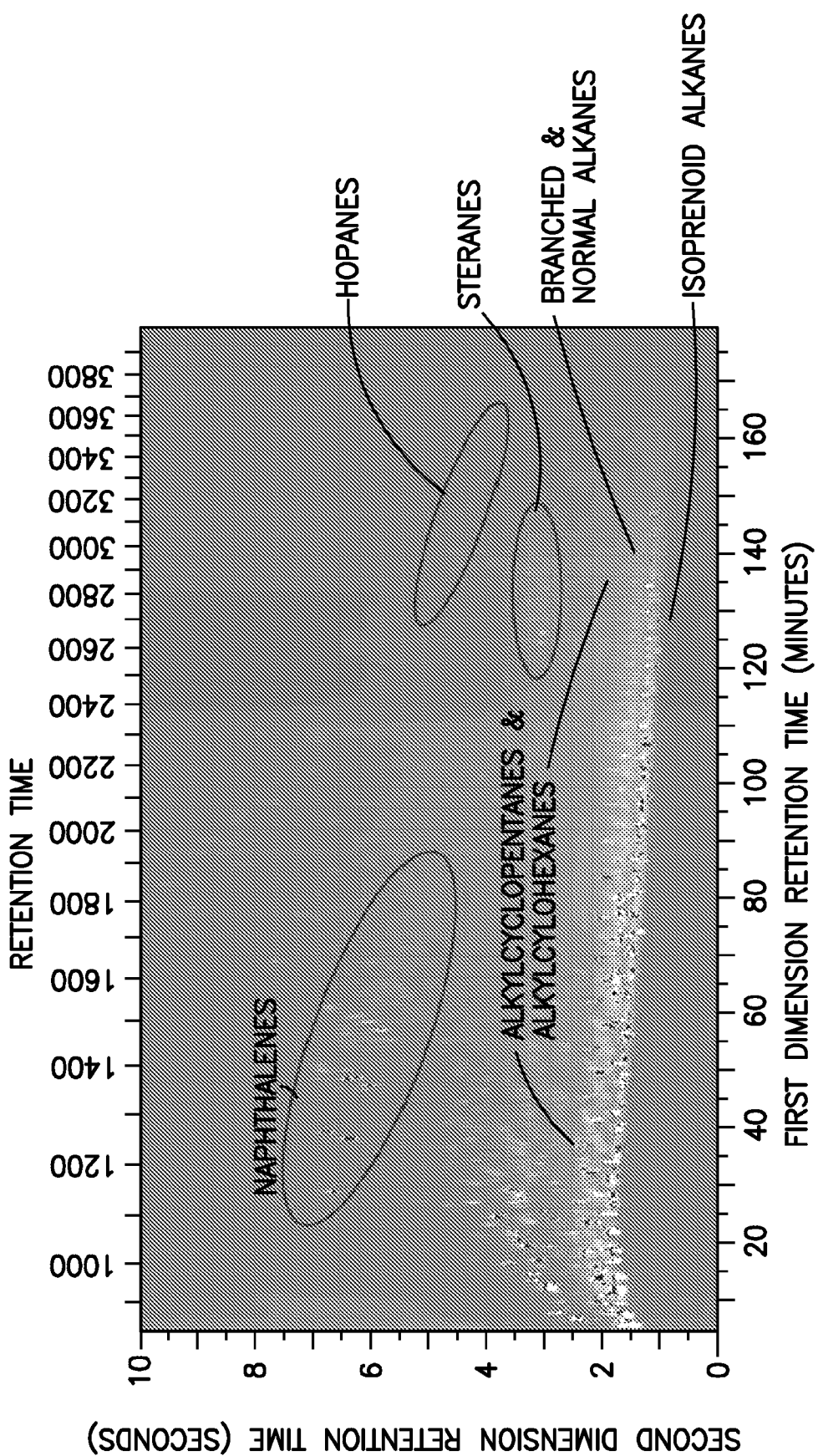
FIG. 2 shows according to an aspect of the invention, the GC×GC-FID grayscale contour chromatogram of a hydrocarbon sample with some petroleum compound classes annotated. The retention index employed is based on the modified Kovats index of Van Den Dool and Kratz, which can be useful for comparing compound retention between samples analyzed under varying temperature programs or between samples analyzed on different gas chromatographs. It can be particularly useful for petroleum samples since the scale is based on n-alkane retention (and then multiplied by 100). For example, the retention index of n-$C_{12}$ and n-$C_{20}$ are 1200 and 2000, respectively.
Figure 3A:
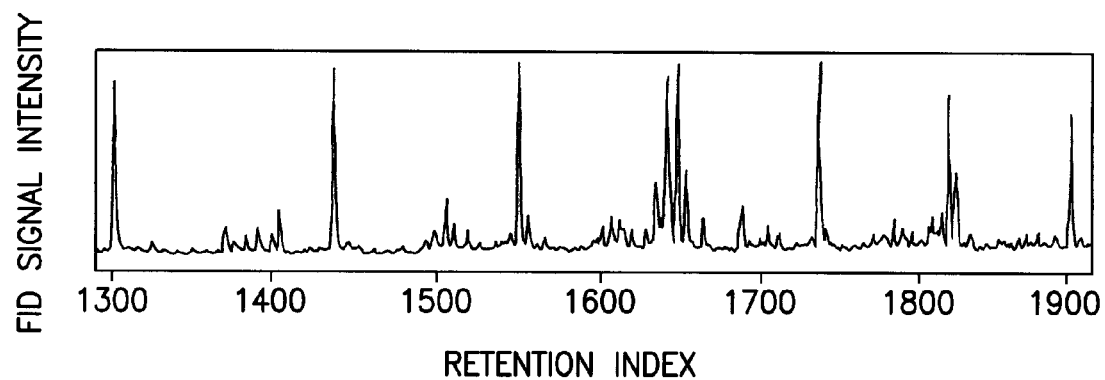
FIGS. 3(a), (b) and (c) shows according to an aspect of the invention, the comparison between 1D-GC and GC×GC-FID. (This is the same sample from FIG. 2 but with a smaller retention window).
Figure 3B:
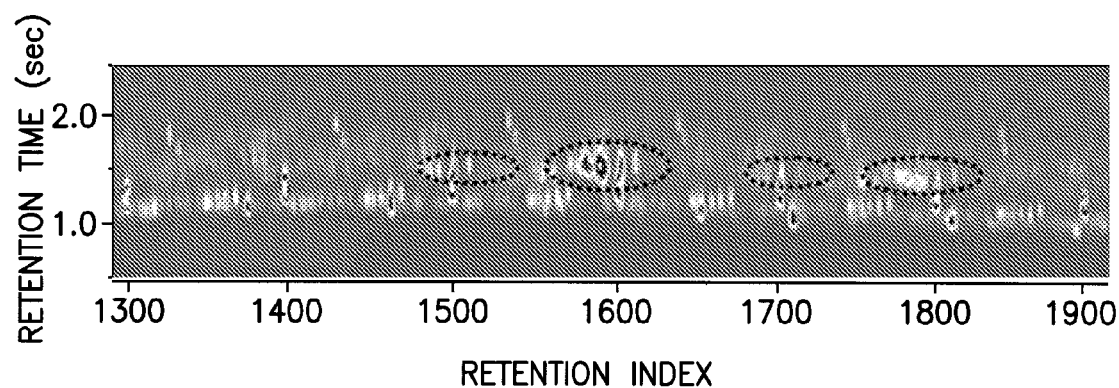
FIG. 3(b) shows the GC×GC-FID of the same sample as (a) but with a smaller retention window. The ovals indicate retention of the alkenes.

FIG. 2 shows the GC×GC–FID chromatogram of a contaminated hydrocarbon sample (although the contamination is difficult to observe because of the wide range used for the X-axis; see FIG. 3b for a zoomed in image of the relevant region) 200. The contamination is due to an internal-olefin based SBM. The data are displayed as a grayscale contour plot, with gray representing low signal and white representing a high signal. In order to visualize the minor peaks, the dynamic range that is plotted is often less than the total dynamic range of the sample, with the tops of the tallest peaks "chopped off." This produces a gray area surrounded by a white area near the center of large peaks.

The GC×GC–FID chromatogram of the contaminated crude oil is based on a first volatility-based separation with a non-polar polydimethylsiloxane column. This produced essentially a boiling point separation of the compounds along the x-axis. A subsequent polarity-based separation with a more polar 50% phenyl-substituted polydimethylsiloxane column produced a chemical class-type separation along the y-axis. In the second dimension, the least polar petroleum class observed in this sample, the branched and n-alkanes have the least retention on the second column, and are located at the bottom of the chromatogram. The most polar classes, multi-ring polyaromatic hydrocarbons (PAHs), have the greatest retention on the second column and are located near the top of the chromatogram. The cycloalkanes appear in bands just above the branched alkanes because the ring structure makes them slightly more polar so they have slightly more retention on the second dimension. The first of the cyclohexane bands contain the numerous one-ring alkylcycloalkanes, including the alkylcyclohexanes and alkylcyclopentanes. Other petroleum components of interest shown in FIG. 2 are the sterane and hopane biomarkers. This type of carbon range as well as distribution and abundance of petroleum components is typical of GC×GC–FID images for crude oils or other heavy oils.

One of the differences between 1D–GC and GC×GC–FID and the possible usefulness of the latter in identifying drilling fluid contamination is shown in FIGS. 3a and 3b chromatograms of the same sample acquired from each respective instrument type. This is the same sample from FIG. 2, but only the contamination-relevant elution window from $n-C_{13}$ to $n-C_{19}$ is shown. To keep track of where each n-alkane elutes in this comparison, the retention index for 1D–GC is at the top of the figure while for GC×GC–FID it is at the bottom.

As shown in FIG. 3, in both the 1D–GC and GC×GC–FID images, we observed the presence of some compounds not typically observed in hydrocarbon samples 300. These compounds are shaded in the FIG. 3a 301 and enclosed within ovals in FIG. 3b 302. It is possible that this is where alkenes from iso-olefin drilling fluids would elute based on GC×GC chromatograms of different lots of commercially produced olefins containing $C_{16}$ to $C_{18}$ alkenes and hypothetical calculations.

This space in GC×GC–FID images is unoccupied in petroleum samples, which is reasonable since alkenes are not generally present in crude oils at such levels. By visual inspection and commercial standards, we were only able to identify three alkene regions in the 1D–GC trace (FIG. 3a), but we were able to highlight four regions of alkenes with pink ovals with GC×GC–FID (FIG. 3b). (While not shown in FIG. 3b, we were also able to identify some $C_{20}$ alkenes by GC×GC–FID but not in 1D–GC). It is also worth noting the increased signal to noise achieved for the alkenes for GC×GC–FID relative to 1D–GC. For example, we could detect alkenes that elute near n-$C_{17}$ (retention index of ~1700) by GC×GC–FID (FIG. 3b) but not in 1D–GC (FIG. 3a).

Figure 3C:
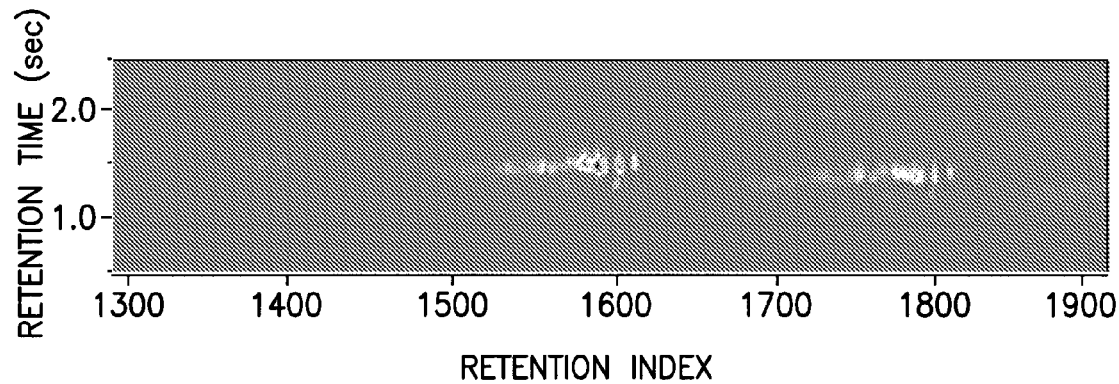
FIG. 3(c) shows the GC×GC-FID of a commercially-available iso-olefin mixture acquired from M-I Drilling Fluids. To help keep track of where each n-alkane elutes in this comparison, the retention index for 1D-GC and the GC×GC-FID are provided at the bottom of each chromatogram.

Finally, when comparing FIGS. 3a to 3b, look at any oval region in FIG. 3b, all of the peaks above or below that oval in the second dimension are co-eluting with the alkenes in first dimension and only the second dimension was able to separate them. Hence, GC×GC–FID is more selective than 1D–GC because of the second dimension separating out any possible co-eluters. For additional evidence, we analyzed by GC×GC–FID a commercial iso-olefin drilling fluid sample that we obtained from M-I Drilling Fluids (FIG. 3c). It is quite clear that the chromatograms from the oil sample (FIG. 3b) and the iso-olefin mixture (FIG. 3c) have the same elution characteristics and both are dominated by $C_{16}$ alkenes and $C_{18}$ alkenes from drilling fluids.

The extremely high resolution of the GC×GC technique allows for clear separation of the alkenes and can hence be used to calculate SBM contamination by summing the peak volumes of the alkenes relative to the rest of the peak volumes of the total petroleum hydrocarbons in the chromatogram. This approach is more selective than other methods and does not rely on any elaborate calibrations or assumptions of exponential relations between $C_8$+ components. It is estimated that contaminations as low as 0.1% can be detected using this technique. This technique will be as effective in highly contaminated samples as well because of similar factors discussed for trace levels. Further, the increased signal-to-noise afforded by GC×GC allows highly contaminated samples to be diluted to such levels that both the petroleum hydrocarbons and the contaminant can be observed and quantified.

gerprinting the diesel or mineral oil used for drilling with GC×GC, one can look for tracers that are in the GC×GC space that are specific to the OBM and generally not present in hydrocarbon.

Figure 5:
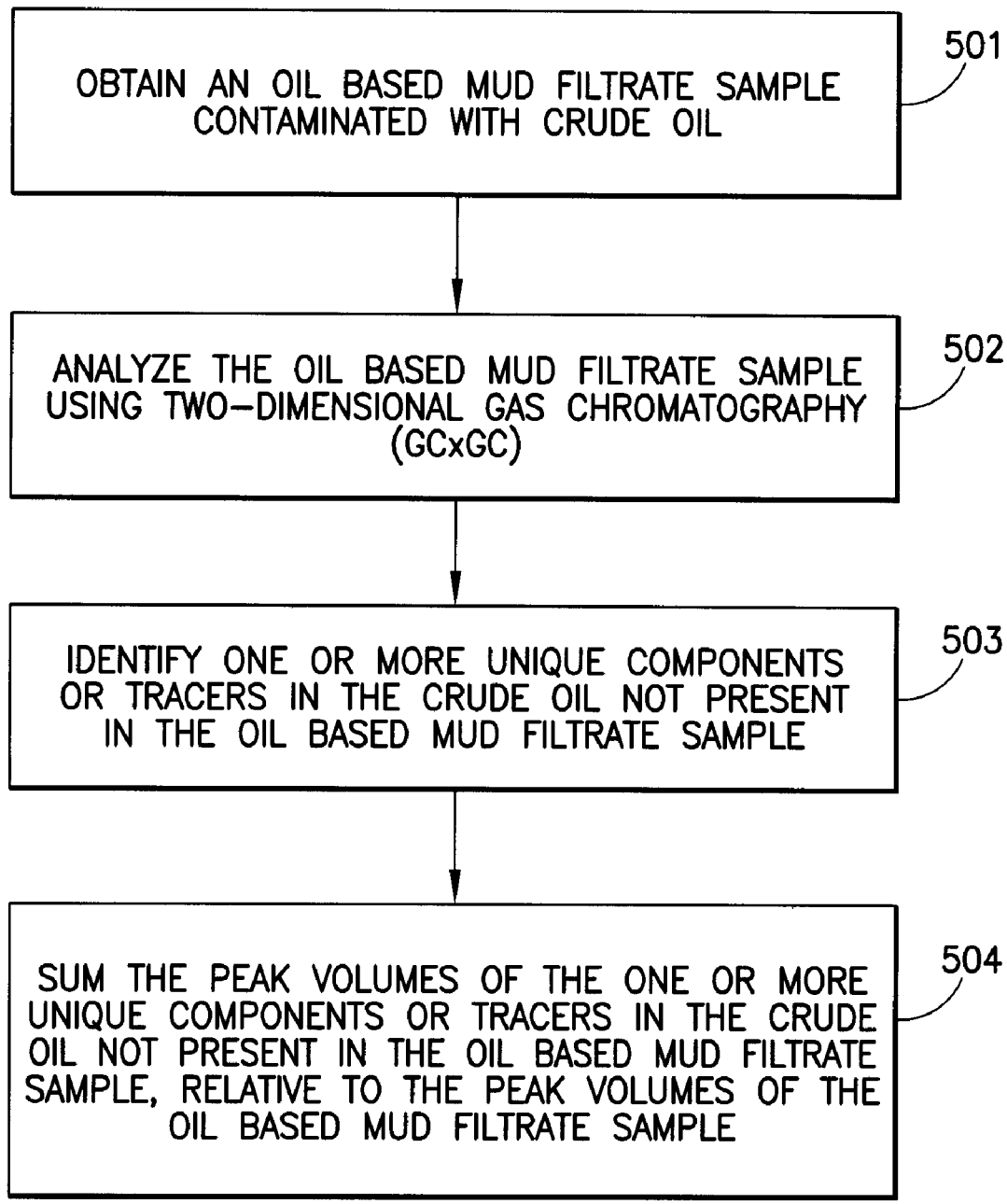
FIG. 5 shows according to an aspect of the invention, a method for estimating the amount of contamination of crude oil in an oil based mud filtrate sample.

Referring to FIG. 5, a method for estimating contamination of crude oil in an oil based mud filtrate sample 500 is shown. First, an oil based mud filtrate sample contaminated with crude oil is obtained 501. Next, the contaminated oil based mud filtrate sample is analyzed using two-dimensional gas chromatography (GC×GC) 502 in order to identify one or more unique components or tracers present in the crude oil but in the oil based mud filtrate sample 503. Finally, the peak volumes of the one or more unique components or tracers in the crude oil are summed, relative to the peak volumes of the oil based mud filtrate sample 504. This method provides an estimate of the contamination of crude oil in the oil based mud filtrate sample.

The high resolving power of GC×GC technique allows for robust detection of these unique components or tracers and hence allows for contamination estimation with higher accuracy than current one-dimensional gas chromatography methods both at low and high levels of contamination. This method does not rely on an exponential relation among $C_8$+ hydrocarbon components and hence is more robust and valid for all complex fluids such as biodegraded or water washed crude oils and the like. The technique can also be used to identify contamination of drilling fluid filtrates by crude oil. This could be important prior to disposal of the drilling fluid, especially for the synthetic drilling fluids.

EXAMPLES

Four crude oil samples contaminated with drilling fluid were obtained from an exploration well (see Table 1 below). They were flashed to remove any volatile components (<n-$C_9$ alkanes) and subjected to a standard asphaltene precipitation. Solutions for analysis were prepared in hexane.

For comparison, we also obtained one iso-olefin fluid and one linear alpha olefin fluid from M-I Drilling Fluids (Houston, Tex., USA).

TABLE 1

Compositional data for alkenes in oil samples by GC × GC-FID and compared to estimates made by integrating alkene peaks via one-dimensional GC-FID

| Sample | Relative amount $C_{15}$-enes in total alkenes (%) | Relative amount $C_{16}$-enes in total alkenes (%) | Relative amount $C_{17}$-enes in total alkenes (%) | Relative amount $C_{18}$-enes in total alkenes (%) | Total alkene content ($C_{15}$-, $C_{16}$-, $C_{17}$- and $C_{18}$-enes) by GC × GC-FID (%) | Total alkene content from ID GC-FID (from integrating the shading areas in FIG. 4 as defined by elution of the commercial iso-olefin mixture and standards) (%) |
|---|---|---|---|---|---|---|
| C | 12.2 | 57.9 | 6.8 | 23.1 | 3.9 | 3.8 |
| F1 | 13.2 | 54.9 | 7.3 | 24.7 | 3.5 | 3.3 |
| F2 | 12.5 | 56.2 | 6.8 | 24.5 | 3.6 | 3.1 |
| B | 14.6 | 50.9 | 8.8 | 25.8 | 1.6 | 1.2 |
| Mean +/− SD | 13.1 +/− 1.0 | 54.9 +/− 3.0 | 7.4 +/− 0.9 | 24.5 +/− 1.1 | | |

Figure 4:
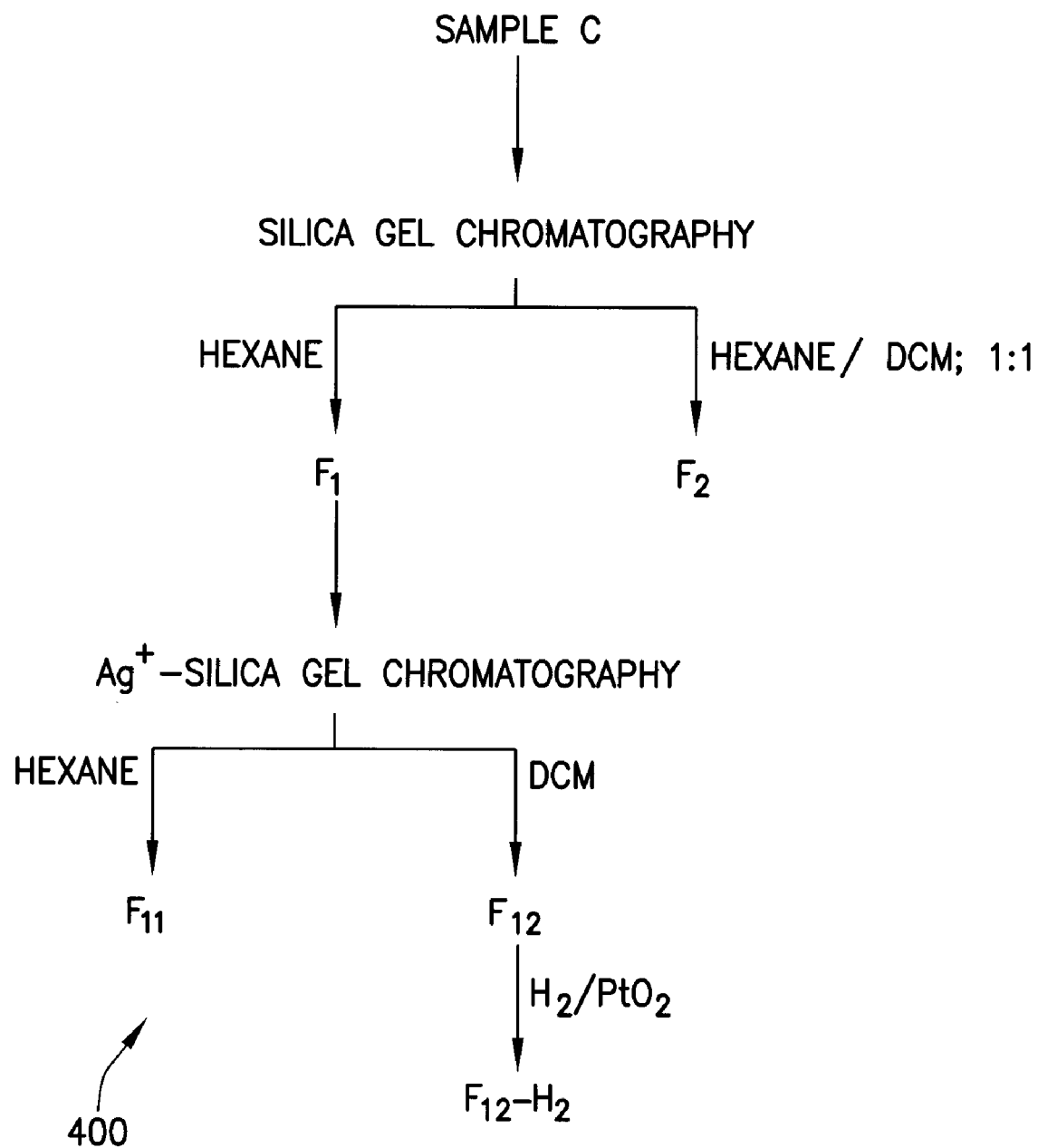
FIG. 4 shows according to an aspect of the invention, a flowchart of separation scheme used to isolate alkenes from other petroleum components in sample C and hydrogenation (Table 1).

While the example discussed here uses internal olefin based SBM, one can apply similar techniques for linear alpha olefins, poly-alpha olefins, and ester-based synthetic mud as these are components not found in hydrocarbons, i.e., crude oil samples. One can also potentially get more accurate results for traditional oil-based muds based on diesel and mineral oil. These muds have a wide spread of carbon numbers and contamination caused by them is more difficult to estimate with one-dimensional gas chromatography. By fin- To isolate an alkene fraction, sample C (Table 1) was subjected to silica gel chromatography and then silver-impregnated silica gel chromatography. Refer to FIG. 4 for a flowchart of this separation scheme 400. Briefly, the sample (~10 mg) was first charged onto a glass column (18 cm×0.5 cm) packed with fully activated silica gel (100-200 mesh). To isolate a saturate and alkene fraction (designated the $F_1$), the column was first eluted with 9 ml of hexane. The column was then eluted with 11 ml of a 1:1 mixture of hexane:dichloromethane (DCM) to isolate aromatics and other more polar materials (designated the $F_2$). To further separate the $F_1$ into saturates and alkenes, the $F_1$ was reduced in volume to ~1 ml and charged onto a glass column (18 cm×0.5 cm) packed with fully activated silver-impregnated silica gel (~10 wt. % $AgNO_3$ on +200 mesh; Sigma—Aldrich; catalog no. 248762-50G). The saturates were eluted with 8 ml of hexane ($F_{11}$) and then the alkenes were eluted with 10 ml of DCM ($F_{12}$). The $F_1$, $F_2$, $F_{11}$ and $F_{12}$ were each analyzed by one-dimensional GC–FID and gas chromatography mass spectrometry (GC-MS) and also GC×GC–FID.

To investigate whether all of the alkenes isolated in the $F_{12}$ fraction of sample C (and also the two drilling fluids) were linear or branched, each sample was hydrogenated. Briefly, 0.5 mg or less of sample was placed in a 25 ml vial that had a Mininert valve/cap. Four millilitres of hexane, 5 mg of $PtO_2$ and a Teflon-coated stir bar were then added. The vial was secured with the cap and then was flushed via the valve through a needle with $H_2$ at about ~60 ml min$^{-1}$ for 10 min. The needle was removed, the valve was closed, and the samples were stirred for 1 h. Each sample was filtered through a glass wool $Na_2SO_4$ column, reduced in volume by rotary evaporation, and stored until analysis. Each was analyzed by one-dimensional GC–FID and GC-MS and also GC×GC–FID.

Samples were analyzed on a Hewlett-Packard 6890 Series gas chromatograph with a cooled injection system (CIS) and interfaced to both a Hewlett-Packard 5973 mass spectrometer and flame ionization detector. A 1 µl sample was injected into the CIS, which was temperature programmed from 50 (0.1 min hold) to 350° C. at 720° C. min$^{-1}$ (8 min hold). Compounds were separated on a fused silica capillary column (J&W DB-5 ms, 60 m length, 0.32 mm inner diameter, 0.25 µm film thickness) with He as the carrier gas at a constant flow of 1.5 ml min$^{-1}$. The GC oven temperature was started at 50° C. (1 min hold) ramped at 20° C. min$^{-1}$ to 115° C. (10 min hold) then ramped 5° C. min$^{-1}$ to 320° C. (10 min hold). A commercially available glass-lined fixed outlet splitter (SGE) was used to split the column effluent to the MS and FID at a ratio of approximately 2:1. The MS was run in the full scan mode from 50 to 800 amu. The MS transfer line was held at 325° C. The FID was held at 325° C. and sampled at 10 Hz.

Each extract was analyzed on a GC×GC–FID that employed a loop-jet modulator, which was purchased from the Zoex Corporation, Lincoln, Nebr. The complete system included an Agilent 6890 gas chromatograph configured with a 7683 series split/splitless auto-injector, two capillary gas chromatography columns and a flame ionization detector. Each extract was injected in splitless mode and the purge vent was opened at 0.5 min. The inlet temperature was 295° C. The first dimension column and the loop jet modulator reside in the main oven of the Agilent 6890 gas chromatograph (Agilent, Wilmington, Del.). The second dimension column is housed in a separate oven installed within the main GC oven. With this configuration, the temperature profiles of the first dimension column, thermal modulator and the second dimension column can be independently programmed. The FID signal was sampled at 100 Hz. The carrier gas was $H_2$ at a constant flow rate of 0.7 ml min$^{-1}$. Peaks were identified with commercially available standards from Aldrich, US National Institute of Standards and Technology (NIST), and Chiron (Chiron, Trondheim, Norway).

We used two different GC×GC temperature-ramp programs in this study. The initial ramp program (Program A) was developed to analyze a mixture containing a broad spectrum of components while Program B was fine tuned to enhance resolution around the compounds of interest that we identified with Program A. In Program A, the first dimension column was a nonpolar 100% dimethylpolysiloxane phase (Restek Rtx-1 Crossbond, 7.5 in length, 0.10 mm inner diameter, 0.1 µm film thickness) that was programmed to remain isothermal at 33° C. for 5 min and then ramped from 33 to 285° C. at 1.5° C. min$^{-1}$. The modulation loop was deactivated fused silica (1.5 in length, 0.10 mm inner diameter). The modulator cold jet gas was dry $N_2$, chilled with liquid Ar, with a constant flow rate of 2.21 min$^{-1}$. The modulator hot jet air was heated to 105° C. above the temperature of the first oven. The hot jet was pulsed for 350 ms every 10 s (0.10 Hz). The modulation period, therefore, was 10 s. Second dimension separations were performed on a 50% phenyl polysilphenylene-siloxane column (SGE BPX50, 2.0 m length, 0.10 mm inner diameter, 0.1 µm film thickness) that was programmed to remain isothermal at 46° C. for 5 min and then ramped from 46 to 298° C. at 1.5° C. min$^{-1}$. In Program B, the same first and second columns were used but the temperature programs of the first and second ovens were modified. The first dimension column oven was programmed to remain isothermal at 70° C. for 15 min and then ramped from 70 to 160° C. at 0.75° C. min$^{-1}$. The modulator hot jet air was heated to 105° C. above the temperature of the first oven. The hot jet was pulsed for 350 ms every 12.5 s (0.08 Hz). Hence, the modulation period was 12.5 s. The second dimension column oven was programmed to remain isothermal at 82° C. for 15 min and then ramped from 82 to 172° C. at 0.75° C. min$^{-1}$.

The GC×GC–FID data were processed with Noesys Research Systems-Transform version 3.4 and GC Image software (Fortner Software LLC, Boulder, Colo. and GC Image, LLC, Lincoln, Nebr., respectively). GC×GC–FID data matrices were rotated to place n-alkane peaks at the bottom of the two-dimensional chromatographic image. Each GC×GC image was base-plane subtracted to remove the FID offset. Individual resolved peaks were automatically identified and integrated by the software. Compound classes were identified and analyzed with user-defined parameters designed to highlight and quantify areas of the GC×GC chromatogram where specific families of compounds elute and collectively integrated as the sum of the individual peaks in the defined area.

It is noted that the foregoing examples have been provided merely for the purpose of explanation and are in no way to be construed as limiting of the present invention. While the present invention has been described with reference to an exemplary embodiment, it is understood that the words, which have been used herein, are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A method of analyzing contamination of oil based mud filtrate in a hydrocarbon sample, the method comprising the steps of:
   a) obtaining a hydrocarbon sample contaminated with oil based mud filtrate wherein the oil based mud filtrate is selected from the group consisting of a non-synthetic oil based mud filtrate or a synthetic oil based mud filtrate;
   b) analyzing the contaminated hydrocarbon sample using two-dimensional gas chromatography (GC×GC);

c) identifying one or more unique component or tracer in the oil based mud filtrate in the contaminated hydrocarbon sample; and d) summing the peak volumes of the one or more unique component or tracer, relative to the peak volumes of a clean hydrocarbon sample.

2. The method of claim 1, wherein at least one unique component of the one or more unique component is from the synthetic oil based component.

3. The method of claim 1, wherein at least one tracer of the one or more tracer is added to the non-synthetic oil based mud filtrate.

4. The method of claim 1, wherein the contamination of oil based mud filtrate in the hydrocarbon sample is greater than about 0.1%.

5. The method of claim 1, wherein the contamination of oil based mud filtrate in the hydrocarbon sample is from about 0.1% to about 10%.

6. The method of claim 1, wherein two-dimensional gas chromatography (GC×GC) has a greater resolving power in identifying one or more unique component and tracer compared to a one-dimensional gas chromatography.

7. The method of claim 1, wherein there are at least two or more dimension separations.

8. The method of claim 1, wherein the GC×GC involves a first dimension separation using a non-polar phase; and a second dimension separation using a polar phase.

9. The method of claim 8, wherein non-polar phase separates petroleum compounds by volatility differences; and the polar phase separates first dimension co-eluters by polarity differences.

10. The method of claim 9, wherein the non-polar phase is a polydimethylsiloxane column; and the polar phase is a 50% phenyl-substituted polydimethylsiloxane column.

11. The method of clam 1, wherein the unique component or tracer in the oil based mud filtrate is selected from the group consisting of an iso-olefin, a liner alpha olefin, a poly-alpha olefin or ester.

12. The method of claim 11, wherein the iso-olefin is a $C_{16}$ to $C_{20}$ alkene.

13. A method of separating and analyzing contamination of drilling fluid in a hydrocarbon sample, the method comprising the steps of:

a) obtaining a hydrocarbon sample contaminated with drilling fluid;

b) analyzing the contaminated hydrocarbon sample using two-dimensional gas chromatography (GC×GC), wherein the contaminated hydrocarbon sample is subject to two different stationary phase selectivities;

c) identifying one or more unique component or tracer in the drilling fluid in the contaminated hydrocarbon sample; and d) summing the peak volumes of the one or more unique component or tracer, relative to the peak volumes of a clean hydrocarbon sample.

14. The method of claim 13, wherein the drilling fluid is selected from the group consisting of an oil based mud filtrate, a non-synthetic oil based mud filtrate, a synthetic oil based mud filtrate or some combination thereof.

15. The method of claim 14, wherein the one or more unique component is from the synthetic oil based mud filtrate.

16. The method of claim 14, wherein the method includes at least one tracer of the one or more tracer that is added to the non-synthetic oil based mud filtrate.

17. The method of claim 13, wherein the two different stationary phase selectivities involves a first dimension separation using a non-polar phase; and a second dimension separation using a polar phase.

18. The method of claim 17, wherein non-polar phase separates petroleum compounds by volatility differences; and the polar phase separates first dimension co-eluters by polarity differences.

19. The method of claim 18, wherein the non-polar phase is a polydimethylsiloxane column; and the polar phase is a 50% phenyl-substituted polydimethylsiloxane column.

20. The method of claim 13, wherein the contamination of drilling fluid in the hydrocarbon sample is greater than about 0.1%.

21. The method of clam 13, wherein the unique component or tracer in the drilling fluid is selected from the group consisting of an iso-olefin, a liner alpha olefin, a poly-alpha olefin or ester.

22. The method of claim 21, wherein the iso-olefin is a $C_{16}$ to $C_{20}$ alkene.

* * * * *

UNITED STATES PATENT AND TRADEMARK OFFICE
CERTIFICATE OF CORRECTION

| | |
|---|---|
| PATENT NO. | : 7,805,979 B2 |
| APPLICATION NO. | : 11/876185 |
| DATED | : October 5, 2010 |
| INVENTOR(S) | : Robert Nelson et al. |

Page 1 of 1

It is certified that error appears in the above-identified patent and that said Letters Patent is hereby corrected as shown below:

In the specification

In Column 1, line 4, before "BACKGROUND OF THE INVENTION" the following should be inserted:

--STATEMENT OF RIGHTS TO INVENTIONS MADE UNDER FEDERALLY SPONSORED RESEARCH
This invention was made with Government support under N00014-04-1-0029 awarded by the Office of Naval Research. The Government has certain rights in this invention.--

Signed and Sealed this
Thirty-first Day of May, 2016

Michelle K. Lee
*Director of the United States Patent and Trademark Office*